United States Patent
Yanagi et al.

(10) Patent No.: US 9,200,314 B2
(45) Date of Patent: Dec. 1, 2015

(54) SYNTHETIC SIRNA DETECTION METHOD

(75) Inventors: Satoshi Yanagi, Shiga (JP); Eiji Kobayashi, Shiga (JP); Takashi Uemori, Shiga (JP); Hiroyuki Mukai, Shiga (JP)

(73) Assignee: TAKARA BIO INC., Otsu-Shi, Shiga (JP)

( * ) Notice: Subject to any disclaimer, the term of this patent is extended or adjusted under 35 U.S.C. 154(b) by 449 days.

(21) Appl. No.: 13/186,941

(22) Filed: Jul. 20, 2011

(65) Prior Publication Data

US 2012/0021420 A1    Jan. 26, 2012

(30) Foreign Application Priority Data

Jul. 21, 2010  (JP) ................................ 2010-164109

(51) Int. Cl.
| | |
|---|---|
| *C12P 19/34* | (2006.01) |
| *C12Q 1/68* | (2006.01) |
| *C12N 15/10* | (2006.01) |
| *C07H 21/02* | (2006.01) |
| *C07H 21/04* | (2006.01) |

(52) U.S. Cl.
CPC .......... *C12Q 1/6806* (2013.01); *C12N 15/1096* (2013.01)

(58) Field of Classification Search
CPC ........... C12Q 1/6806; C12Q 2525/173; C12Q 2525/207; C12N 15/1096
See application file for complete search history.

(56) References Cited

U.S. PATENT DOCUMENTS

| | | |
|---|---|---|
| 2009/0220969 A1 | 9/2009 | Chiang et al. |
| 2010/0279305 A1* | 11/2010 | Kuersten ........................... 435/6 |
| 2011/0033858 A1 | 2/2011 | Futami et al. |

FOREIGN PATENT DOCUMENTS

| | | |
|---|---|---|
| JP | 2007-532100 A | 11/2007 |
| WO | 2005098029 A2 | 10/2005 |
| WO | WO 2005/098029 * | 10/2005 |
| WO | 2009/098988 | 8/2009 |

OTHER PUBLICATIONS

Futami, K. et al., Anal. Biochem., vol. 385, pp. 386-388 (2009).*
Biggs, P.J. et al., Biochemoca, No. 4, pp. 18-21 (2005).*
Ro et al., Biochem. Biophys. Res. Comm., vol. 351, pp. 756-763 (2006).*
Stratagene Catalog, p. 39 (1988).*
Notification of Reasons for Refusal (drafted on Aug. 12, 2015) in the corresponding Japanese patent application (Application No. 2011-159482) and English translation thereof.

* cited by examiner

*Primary Examiner* — Teresa E Strzelecka
(74) *Attorney, Agent, or Firm* — Banner & Witcoff, Ltd.

(57) ABSTRACT

A method for accurately and easily detecting a synthetic siRNA, for example, a siRNA in which the 3' end is DNA, and a kit used for the method are provided. The present invention relates to a method for detecting a siRNA in which the 3' end is DNA, comprising: (a) adding polydeoxyadenosine to the 3' DNA end of at least one strand of the siRNA to be detected to produce a polydeoxyadenosine-added RNA; (b) annealing a polydeoxythymidine primer having a tag sequence at its 5' side to the polydeoxyadenosine-added RNA and synthesizing DNA from the primer by a reverse transcription; and (c) detecting the DNA synthesized in (b).

5 Claims, 4 Drawing Sheets

SEQUENCE LISTING

```
<160> NUMBER OF SEQ ID NOS: 13

<210> SEQ ID NO 1
<211> LENGTH: 21
```

```
<212> TYPE: DNA
<213> ORGANISM: Artificial
<220> FEATURE:
<223> OTHER INFORMATION: Synthetic oligonucleotide GL3-siRNA.
      Nucleotides 1 to 19 are ribo nucleotides-other nucleotides are
      deoxyribonucleotides.

<400> SEQUENCE: 1
ucgaaguacu cagcguaagt t                                              21

<210> SEQ ID NO 2
<211> LENGTH: 21
<212> TYPE: DNA
<213> ORGANISM: Artificial
<220> FEATURE:
<223> OTHER INFORMATION: Synthetic oligonucleotide GL3-siRNA.
      Nucleotides 1 to 19 are ribo nucleotides-other nucleotides are
      deoxyribonucleotides.

<400> SEQUENCE: 2
cuuacgcuca guacuucgat t                                              21

<210> SEQ ID NO 3
<211> LENGTH: 43
<212> TYPE: DNA
<213> ORGANISM: Artificial
<220> FEATURE:
<223> OTHER INFORMATION: poly dA primer with tag sequence.

<400> SEQUENCE: 3
ggccacgcgt cgactagtat tttttttttt tttttttttt ttt                      43

<210> SEQ ID NO 4
<211> LENGTH: 19
<212> TYPE: DNA
<213> ORGANISM: Artificial
<220> FEATURE:
<223> OTHER INFORMATION: Tag sequence primer.

<400> SEQUENCE: 4
ggccacgcgt cgactagta                                                 19

<210> SEQ ID NO 5
<211> LENGTH: 19
<212> TYPE: DNA
<213> ORGANISM: Artificial
<220> FEATURE:
<223> OTHER INFORMATION: Antisense primer for GL3-siRNA.

<400> SEQUENCE: 5
cttacgctca gtacttcga                                                 19

<210> SEQ ID NO 6
<211> LENGTH: 36
<212> TYPE: DNA
<213> ORGANISM: Artificial
<220> FEATURE:
<223> OTHER INFORMATION: poly dC primer with tag sequence.

<400> SEQUENCE: 6
ggccacgcgt cgactagtac cccccccccc cccccc                              36

<210> SEQ ID NO 7
<211> LENGTH: 21
<212> TYPE: DNA
<213> ORGANISM: Artificial
<220> FEATURE:
```

```
<223> OTHER INFORMATION: Synthetic oligonucleotide PLK1-siRNA.
      Nucleotides 1 to 19 are ribonucleotides-other nucleotides are
      deoxyribonucleotides.

<400> SEQUENCE: 7
ccuugaugaa gaagaucact t                                              21

<210> SEQ ID NO 8
<211> LENGTH: 21
<212> TYPE: DNA
<213> ORGANISM: Artificial
<220> FEATURE:
<223> OTHER INFORMATION: Synthetic oligonucleotide PLK1-siRNA.
      Nucleotides 1 to 19 are ribonucleotides-other nucleotides are
      deoxyribonucleotides.

<400> SEQUENCE: 8
gugaucuucu ucaucaaggt t                                              21

<210> SEQ ID NO 9
<211> LENGTH: 21
<212> TYPE: DNA
<213> ORGANISM: Artificial
<220> FEATURE:
<223> OTHER INFORMATION: Synthetic oligonucleotide MetLuc-siRNA.
      Nucleotides 1 to 19 are ribonucleotides-other nucleotides are
      deoxyribonucleotides.

<400> SEQUENCE: 9
ccauggaagu gaugaucaat t                                              21

<210> SEQ ID NO 10
<211> LENGTH: 21
<212> TYPE: DNA
<213> ORGANISM: Artificial
<220> FEATURE:
<223> OTHER INFORMATION: Synthetic oligonucleotide MetLuc-siRNA.
      Nucleotides 1 to 19 are ribonucleotides-other nucleotides are
      deoxyribonucleotides.

<400> SEQUENCE: 10
uugaucauca cuuccauggt t                                              21

<210> SEQ ID NO 11
<211> LENGTH: 19
<212> TYPE: DNA
<213> ORGANISM: Artificial
<220> FEATURE:
<223> OTHER INFORMATION: Antisense primer for PLK1-siRNA

<400> SEQUENCE: 11
gtgatcttct tcatcaagg                                                 19

<210> SEQ ID NO 12
<211> LENGTH: 19
<212> TYPE: DNA
<213> ORGANISM: Artificial
<220> FEATURE:
<223> OTHER INFORMATION: Antisense primer for MetLuc-siRNA

<400> SEQUENCE: 12
ttgatcatca cttccatgg                                                 19

<210> SEQ ID NO 13
<211> LENGTH: 45
<212> TYPE: DNA
<213> ORGANISM: Artificial
```

```
<220> FEATURE:
<223> OTHER INFORMATION: Oligo dT primer(AA)

<400> SEQUENCE: 13
ggccacgcgt cgactagtat tttttttttt tttttttttt tttaa          45
```

SYNTHETIC SIRNA DETECTION METHOD

This application is based on Japanese Patent Application No. P2010-164109, filed on Jul. 21, 2010, the entire contents thereof being hereby incorporated by reference.

FIELD OF THE INVENTION

The present invention relates to a method for detecting a siRNA in which the 3' end is DNA, and a kit used for the method.

BACKGROUND

Recently, genetic engineering techniques using small molecule double stranded RNA (dsRNA) have been reported.

RNA interference (RNAi) known as a representative technique thereof is a phenomenon in which mRNA is degraded nucleotide-sequence-specifically by dsRNA, and the expression of a polypeptide encoded by the mRNA is suppressed. The fact that genes are silenced by dsRNA was initiated by study on antisenses in nematodes. In 1998, Fire et al. found that dsRNA is a trigger of gene silencing, antisense RNA and sense RNA are not capable of suppressing the expression of genes, and dsRNA in which antisense and sense RNA strands are annealed can efficiently suppress the expression of genes. In the RNA interference, an enzyme called Dicer produces small interfering RNA (siRNA) from the dsRNA.

This biological phenomenon which takes place in the cytoplasm of a cell is widely used as a tool for molecular biological studies and for the purpose of drug discovery research that screens a target protein of a drug. Also, dsRNA artificially sent into cells can strictly suppress the copy number of a specific protein, even at a low concentration. Thus, drug development which attempts to utilize dsRNA as a nucleic acid pharmaceutical is being progressed.

In terms of suppression of interferon responses in a mammalian cell, dsRNA (siRNA) consisting of single stranded RNA with a length of conventionally 15 to 25 base pairs is selected as the synthetic dsRNA. In addition, dsRNA in which 2 to 4 bases are projected on the 3' end side of each strand is frequently used. Furthermore, dsRNA, in which the projected end portion is thymine (T), particularly deoxythymidine (dT), is frequently used.

In order to develop dsRNAs as pharmaceuticals, the explanation of in vivo kinetics (distribution into tissues, metabolic rate, etc.) should be sought. However, detection and measurement technologies for small molecule RNA of a specific molecular species have not been yet established.

A method for detecting siRNA in which its projected end portion consists of DNA, that is, the 3' end is DNA, has been developed, which includes adding polydeoxyguanosine (poly dG) to the 3' end DNA of siRNA using a terminal deoxynucleotidyl transferase (TDT); synthesizing cDNA by reverse transcription reaction using a polydeoxycytidine (poly dC) primer that anneals to the produced poly dG portion; and subsequently performing PCR (e.g., Patent Document 1). In Patent Document 1, the poly dG is considered preferable as a nucleotide added to the 3' end of siRNA, which can be distinguished from the poly A tail of endogenous mRNA. In order to detect a trace of siRNA from mRNA that is abundantly present in biological samples, such as cells, etc., it is known that the addition of polydeoxyadenosine (poly dA) to the 3' end of siRNA should be avoided. Furthermore, in the same document, it is described that poly dG is preferable because, when poly dC or polydeoxythymidine (poly dT) is added to the 3' end of siRNA, it is difficult to control the length of a tailed strand.

[Patent Document 1] International Publication No. WO 2009/098988

BRIEF SUMMARY

An object of the present invention is to provide a method for accurately and easily detecting synthetic siRNA, for example, siRNA in which the 3' end is DNA, and a kit used for the method.

The inventors of the present invention have earnestly studied in order to solve the above problems. The inventors of the present invention developed a method for specifically, accurately and easily detecting siRNA in which the 3' end is DNA, even under the massive presence of mRNA, by adding poly dA to the 3' end of the siRNA.

The present invention includes the following embodiments.

[1] A method for detecting a siRNA in which the 3' end is DNA, comprising:
(a) adding polydeoxyadenosine to the 3' DNA end of at least one strand of the siRNA to be detected to produce a polydeoxyadenosine-added RNA;
(b) annealing a polydeoxythymidine primer having a tag sequence at its 5' side to the polydeoxyadenosine-added RNA and synthesizing DNA from the primer by a reverse transcription; and
(c) detecting the DNA synthesized in (b).

[2] The method of [1], wherein the synthesized DNA is detected by a nucleic acid amplification in (c).

[3] The method of [1] or [2], wherein the synthesized DNA is quantified in (c) to calculate an amount of the siRNA in (a).

[4] The method of any one of [1] to [3], wherein the polydeoxyadenosine is added by a terminal deoxynucleotidyl transferase.

[5] The method of [2], wherein PCR is performed in (c), using the synthesized DNA as a template, and using a primer comprising a sequence homologous to the tag sequence and a primer comprising a sequence homologous to the strand of the siRNA to which the polydeoxyadenosine is added.

[6] The method of [1], wherein the polydeoxythymidine primer having a tag sequence at its 5' side comprises a sequence complementary to the DNA sequence at the 3' end of the siRNA, a polydeoxythymidine sequence, and the tag sequence, in a direction from the 3' end to the 5' end.

[7] A kit for detecting a siRNA in which the 3' end is DNA, comprising dATP, a terminal deoxynucleotidyl transferase, a reverse transcriptase, a polydeoxythymidine primer having a tag sequence at its 5' side, and a primer comprising a sequence homologous to the tag sequence.

According to the present invention, it is possible to specifically and easily detect synthetic siRNA in which the 3' end is DNA, and also measure its amount.

DETAILED DESCRIPTION OF THE INVENTION

As used herein, "siRNA" refers to RNA having a double stranded region of 10 to 50 base pairs, and commonly has a phosphate group at its 5' end and a hydroxyl group at its 3' end. Smooth ends are formed at the ends, or the ends have 1 to 4 base projected 3' end(s). Generally, chemically synthesized siRNA often has a structure in which DNA is projected at the 3' end (overhang), and DNA of the projected portion is frequently a deoxythymine residue (dT). The siRNA is not limited by preparation methods thereof, and includes any siRNA artificially synthesized by chemical synthesis or biochemical methods or produced in the living body.

As used herein, "having at its 5' side" means that any specific sequence region is present preferentially towards the 5' end from the middle of the whole sequence. "Having at its 3' side" is the opposite to the above.

As used herein, the "tag sequence" refers to a sequence established in order to easily screen for a molecule having the tag sequence from a molecule without the tag sequence in various assays. The tag sequence is not particularly limited, as long as it has a strand length and sequence appropriate for the purpose of the present invention, and any sequence can be used. For example, a number of sequence primers and vectors including such sequence primers are commercially available, and a target sequence of primers thereof can be used as a tag sequence.

(1) A Method for Detecting siRNA

The present invention relates to a method for detecting a siRNA in which the 3' end is DNA, comprising the following (a) to (c), (a) adding polydeoxyadenosine (poly dA) to the 3' DNA end of at least one strand of the siRNA to be detected to produce a polydeoxyadenosine-added RNA;
(b) annealing a polydeoxythymidine (poly dT) primer having a tag sequence at its 5' side to the polydeoxyadenosine-added RNA and synthesizing DNA from the primer by a reverse transcription; and
(c) detecting the DNA synthesized in (b).

The siRNA detected by the method according to an exemplary embodiment of the present invention is siRNA in which the 3' end is DNA. The type and number of bases of DNA included in siRNA is not particularly limited, and any base, such as dA, dT, dC, dG, and dU, can be used, and the number of bases may be 1 to 4 bases, and preferably 2 bases. The DNA portion at the 3' end of siRNA may form a projected portion, or a smooth end. It is possible to detect any siRNA with a method according to an exemplary embodiment of the present invention as long as the 3' end is DNA. In an exemplary embodiment of the present invention, the length of the siRNA to be detected is not particularly limited. However, siRNA with, for example, 10 to 100 bases, preferably 15 to 50 bases, and particularly preferably 19 to 30 bases can be detected.

Generally, chemically synthesized siRNA often has a structure in which dT is projected at the 3' end, and in the method according to an exemplary embodiment of the present invention, such a siRNA can be suitably detected. Furthermore, the length of the bases constituting an overhang is not particularly limited, but is usually one to four bases, and is preferably two bases. The bases constituting an overhang may all be DNA. Alternatively, if the 3' end is DNA, other bases than the 3' end may be RNA. In the present invention, the method is preferably a method for detecting siRNA with a structure in which the overhang at the 3' end is two dT bases.

According to the method of an exemplary embodiment of the present invention, siRNA at 2 fM to 200 nM, and particularly 20 fM to 2 nM, can be measured accurately and easily.

The kinetics of siRNA administered to cells or the living body can be investigated by detecting siRNA in a sample derived from the cells or the living body with the method according to an exemplary embodiment of the present invention. It has been difficult to detect siRNA exactly because it is short double-stranded RNA and the concentration distributed in body fluids or organs is low. In the method according to an exemplary embodiment of the present invention, siRNA distributed in cells, tissues, organs, and body fluids, can be detected qualitatively and further quantitatively, even in a sample including large amounts of RNA, such as mRNA, tRNA, and rRNA by using DNA at the 3' end as an index and differentiating the siRNA from them.

<Step (a)>

In the step (a), poly dA is added to the 3' DNA end of at least one strand of siRNA to be detected to produce poly dA-added siRNA. The length of the poly dA to be added is not particularly limited, but is, for example, ten to thirty bases, and is preferably fifteen to twenty five bases. The poly dA is added by a poly dA tailing reaction using an enzyme having an activity to add adenosine triphosphate (dATP) to the DNA end. For example, a tailing reaction can be carried out by using terminal deoxynucleotidyl transferase (TDT) and dATP. The tailing reaction of the poly dA by TDT is carried out by appropriately regulating the concentration of the enzyme and the composition of the reaction buffer according to origin of the TDT and the length of poly dA to be added, and desired reaction conditions are recommended in commercially available TDT.

In addition, in the step (a), poly dA may be added to double-stranded siRNA or poly dA may be added to at least one strand of siRNA dissociated in the form of single strand(s).

<Step (b)>

In the step (b), the poly dA-added RNA produced by the step (a) is used as a template, a poly dT primer having a tag sequence at its 5' side is annealed, followed by reverse transcription reaction from the primer to synthesize DNA. The poly dT primer having a tag sequence at its 5' side has a poly dT sequence region and a tag sequence region, in a direction from the 3' end to the 5' end. The primer can further have any sequence at the 3' end and the 5' end of each region.

The poly dT sequence region is a homopolymer of deoxythymidine, and is annealed to a poly dA sequence region of the poly dA-added siRNA. The whole poly dT sequence region does not need to be annealed to the poly dA, and some of the poly dA region and/or some of the poly dT sequence region may be annealed as long as reverse transcription reaction can be performed. The length of the bases of the poly dT sequence region is, for example, 5 to 40 bases, and preferably 10 to 30 bases.

In an exemplary embodiment of the present invention, a primer further having a sequence complementary to the DNA sequence including the 3' end of siRNA at the 3' end of the poly dT sequence region can be used. That is, a primer including a sequence complementary to the DNA at the 3' end of the siRNA to be detected, a poly dT sequence, and a tag sequence, in the direction from the 3' end to the 5' end, can be used. For example, a siRNA having a structure in which two dT bases are projected at the 3' end, a sequence complementary to the DNA sequence of the siRNA is dA-dA. A position of the poly dA-added siRNA to which such primer is annealed is determined, and the specificity of the subsequent reverse transcription reaction is enhanced.

The length and the line of bases of the tag sequence are not particularly limited, but the tag sequence has preferably a length enough to be used as a primer for PCR because the tag sequence is homologous to the sequence of a primer used in the step (c) subsequent to the step (b). For example, the length of bases of the tag sequence is about 10 to 30 bases, and preferably about 15 to 25 bases. Generally, the tag sequence is preferably a sequence which does not have a sequence homologous to the sequence of siRNA to be detected nor a self-complementary sequence.

The poly dT primer having a tag sequence at its 5' side serves as a primer of reverse transcription reaction, with the poly dT sequence region is annealed to the dA region of the poly dA-added siRNA in the step (a), and DNA is elongated from the 3' end of the primer using a strand of the poly dA-added siRNA as a template. The annealing of the poly dT primer having a tag sequence at its 5' side and the poly dA-added siRNA can be appropriately carried out by a general technique, and can be carried out, for example, by maintaining it at 70° C. for 10 minutes, followed by ice cooling.

Reverse transcription reaction can be appropriately carried out by those skilled in the art according to a general technique using a reverse transcriptase, and the kind thereof is not particularly limited. Any reverse transcriptase can be used as long as it has a reverse transcription activity, that is, an activity to synthesize DNA complementary to RNA as a template, and examples of the reverse transcriptase include a virus-derived reverse transcriptase, such as moloney murine leukemia virus (MMLV)-derived reverse transcriptase and avian myeloblastosis virus-derived reverse transcriptase (AMV)-derived reverse transcriptase, or an eubacteria-derived heat resistant reverse transcriptase, such as Thermus bacteria-derived DNA polymerase (Tth DNA polymerase and the like) and Bacillus bacteria-derived DNA polymerase (Bca DNA polymerase and the like). Commercially available reagents, kits, and the like for reverse transcription reaction may be used appropriately.

Reaction conditions for reverse transcription reaction can be appropriately determined according to the reverse transcriptase to be used. For example, when MMLV-derived reverse transcriptase is used, the reaction can be performed under conditions maintaining the sample at 42° C. for 60 minutes. In addition, after reverse transcription reaction, the reverse transcriptase can be deactivated. The deactivation of the reverse transcriptase is performed by heat treatment or chemical treatment. Heat treatment can be performed when a heat-labile reverse transcriptase is used, and is performed for example at 85° C. for 5 minutes. The chemical treatment can be performed by methods known in the art, for example, phenol-chloroform treatment, and the like.

DNA with a structure including cDNA corresponding to a strand of siRNA, poly dT, and the tag sequence is synthesized in the direction from the 3' end to the 5' end by the reverse transcription reaction as described above.

<Step (c)>

The step (c) is a step for detecting the DNA synthesized in the step (b). The method of detecting DNA can employ general techniques known in the art. When the synthesized DNA derived from siRNA is detected in the present step, it can be shown that siRNA is present in a sample applied by an exemplary embodiment of the present invention. Furthermore, the amount of siRNA present in the sample can be determined by detecting and quantifying the synthesized DNA. For example, the detection of the synthesized DNA can be performed by nucleic acid amplification. A nucleic acid amplification reaction using the DNA as a template can be performed to investigate whether the amplification products are present and to detect siRNA. In addition, the amount of siRNA used in the step (a) can be calculated based on the amount of the amplification product and the amplification efficiency. That is, an exemplary embodiment of the present invention provides a method for qualitatively and quantitatively detecting siRNA in a sample.

As the nucleic acid amplification, any technologies well known in the art may be used, such as, polymerase chain reaction (PCR), isothermal and chimeric primer-initiated amplification of nucleic acids (ICAN), loop mediated isothermal amplification (LAMP), nucleic acid sequence-based amplification (NASBA), strand displacement amplification (SDA), ligase chain reaction (LCR), rolling circle amplification method (RCA method), and transcription mediated amplification (TMA).

Herein below, PCR is described as an example. Generally, PCR is performed by using a primer pair that anneals to the terminal regions of DNA as a template. It is possible to perform PCR using the single-stranded or double-stranded DNA as a template. The primer for amplifying DNA can be easily designed and synthesized by those skilled in the art based on the sequence information of DNA as a template. As an exemplary embodiment of the present invention, a primer pair consisting of, for example, a primer including a sequence homologous to the tag sequence and a primer including a sequence homologous to a strand of siRNA to which poly A is added can be used. Examples of the sequence homologous to the strand of siRNA to which poly dA is added include a sequence homologous to the full length of the strand of siRNA to which poly dA is added and a sequence homologous to a part thereof. For example, when a sense strand of siRNA is detected, a sense strand-specific primer having a sequence in which rA is substituted with dA, rG is substituted with dG, rC is substituted with dC, and rU is substituted with dT in the sense strand sequence or some of the sequence except for the DNA sequence at the 3' overhang can be used. Likewise, when the antisense strand of siRNA is detected, an antisense strand-specific primer having a sequence in which rA is substituted with dA, rG is substituted with dG, rC is substituted with dC, and rU is substituted with dT in the antisense sequence or some of the sequence except for the DNA sequence at the 3' overhang can be used. It is possible to detect siRNA sequence-specifically by using such a primer specific to the siRNA. In addition, either or both of these sense strand and antisense strand specific primers can be used.

As used herein, "a homologous sequence" refers to the same or similar sequence. Generally, an oligonucleotide serving as a primer in PCR anneals to a template and DNA can be elongated from the 3' end thereof, and it is important that the 3' end of the primer anneals to the template. That is, it is known in the art that the primer and the template do not need to be completely annealed. In the present specification, any sequence homologous to a certain sequence is a sequence that can anneal to a sequence complementary to the certain sequence. For example, sequences including a few bases that are not complementary among of 20 bases are homologous when they are annealed. A method for confirming whether sequences are annealed to each other is generally known in the art. A number of software for designing a primer have been developed, and whether sequences can be annealed to each other can be easily predicted. In addition, it can be easily confirmed whether oligonucleotides are actually synthesized and annealed.

When the production of a DNA fragment (amplified product) is detected by the PCR, it is determined that a target siRNA is present in a sample to be tested. PCR and the detection of amplified products can be performed by known techniques, and commercially available reagents, kits, and the like may be used appropriately.

Quantitative PCR, particularly real-time PCR, can be used in the PCR. For example, it is possible to quantify the amounts of siRNA to be detected in a sample based on a calibration curve prepared from the amounts of DNA amplified or Ct values by applying a method according to an exemplary embodiment of the present invention to known amounts of siRNA. In real-time PCR, methods using intercalaters and methods using probes (Taqman probe, cycling probe, and the like) are known, and any method can be used in the present invention. These PCR are techniques well known in the art, and commercially available reagents, kits, and the like may be used appropriately.

Methods for detecting DNA in the step (c) include measurement with a detection probe (Dot-Blot Hybridization method, Southern hybridization method, and the like), detection by array analysis, and the like, in addition to the nucleic acid amplification. In addition, DNA synthesized by using the tag sequence in the step (b) can be detected by general nucleic acid detection methods, e.g., electrophoresis.

(2) Kit for Detecting siRNA

The present invention provides a kit for performing the detection method in (1). The kit includes a dATP, a TDT, a reverse transcriptase, a poly dT primer having a tag sequence at its 5' side, and a primer including a sequence homologous to the tag sequence.

A kit according to an exemplary embodiment of the present invention also may include reagents used in the detection method according to an exemplary embodiment of the present invention. For example, kits including a TDT reaction buffer, a reverse transcriptase reaction buffer, and an RNase Inhibitor may be provided. A TDT reaction buffer including dATP is preferred. Besides the reagents, the kit may further include a siRNA as a control, a primer including a sequence homologous to a strand of siRNA as a control, instructions, and like.

The kit according to an exemplary embodiment of the present invention may include reagents for detection of DNA used in the step (c) in (1). Examples of the reagents include DNA polymerase useful for nucleic acid amplification and reaction buffers thereof.

Herein below, exemplary embodiments of the present invention are described with reference to Examples. However, the technical scope of the present invention is not to be construed as being limited to these Examples.

Example 1

Comparison with Methods for Quantifying Synthetic siRNA Using a Poly dG Addition Reaction A method for quantifying artificially synthesized siRNA using a poly dG addition reaction, which has been reported as a method for quantifying synthetic siRNA, and a method of the present invention were compared with each other.

(1) Manufacture of siRNA

A solution of GL3-siRNA (manufactured by Takara Bio Inc.) including two RNA strands consisting of sequences represented by SEQ ID NOs: 1 and 2, was prepared at 200 nM. In the siRNA, two bases at the 3' ends are dT, and the others are ribonucleotides. The siRNA solution was 10-fold diluted step-by-step until 2 fM.

(2) DNA Addition Reaction

A deoxynucleotide addition reaction to the 3' end of synthetic siRNA by TDT was performed. A poly dA can be added to using dATP in the substrate of the reaction, and a poly dG can be added by using deoxyguanosine 3 phosphate (dGTP).

A reaction solution (25 µL) including 5 µL of siRNA solution at each concentration prepared in Example 1-(1), 1 µL of 14 U/µL TDT (manufactured by Takara Bio Inc.), 5 µL of a 5×TDT buffer attached, 5 µL of 10 mM dATP or dGTP (manufactured by Takara Bio Inc.), and 1 µL of 40 U/µL Recombinant RNase Inhibitor (manufactured by Takara Bio Inc.) was prepared and allowed it to stand at 37° C. for 30 minutes.

(3) Reverse Transcription Reaction

To 5 µL of the reaction solution subjected to poly dA addition reaction in Example 1-(2), 5 µL of 6 µM oligo dT primer (SEQ ID NO: 3) was added to make 10 µL of the mixed solution as a total volume, the resulting solution was subjected to heat treatment at 70° C. for 5 minutes, and rapidly cooled on ice for annealing. The oligo dT primer has a poly dT sequence region of 24 bases at the 3' end and a tag sequence for PCR amplification at the 5' end.

Separately, 5 µL of 6 µM olig dC primer (SEQ ID NO: 6) was added to the reaction solution subjected to poly dG addition reaction in Example 1-(2) and annealed in the same manner. The oligo dC primer has a poly dC region of 17 bases at the 3' end and a tag sequence for PCR amplification at the 5' end.

The annealed reaction solution was subjected to reverse transcription reaction at 42° C. for 15 minutes by using PrimeScript (trademark) RT reagent Kit (Perfect Real Time) (manufactured by Takara Bio Inc.), and a single stranded DNA was synthesized under conditions allowing reverse transcriptase to be deactivated at 85° C. for 5 seconds.

(4) Amplification and Detection of siRNA

Real-time PCR was performed by using SYBR Premix Ex Taq (trademark) (Perfect Real Time) (manufactured by Takara Bio Inc.) and using the DNA prepared in Example 1-(3) as a template. A tag sequence primer (SEQ ID NO: 4) and an antisense-strand derived primer (SEQ ID NO: 5) were used for amplification of the PCR.

Figure 1:
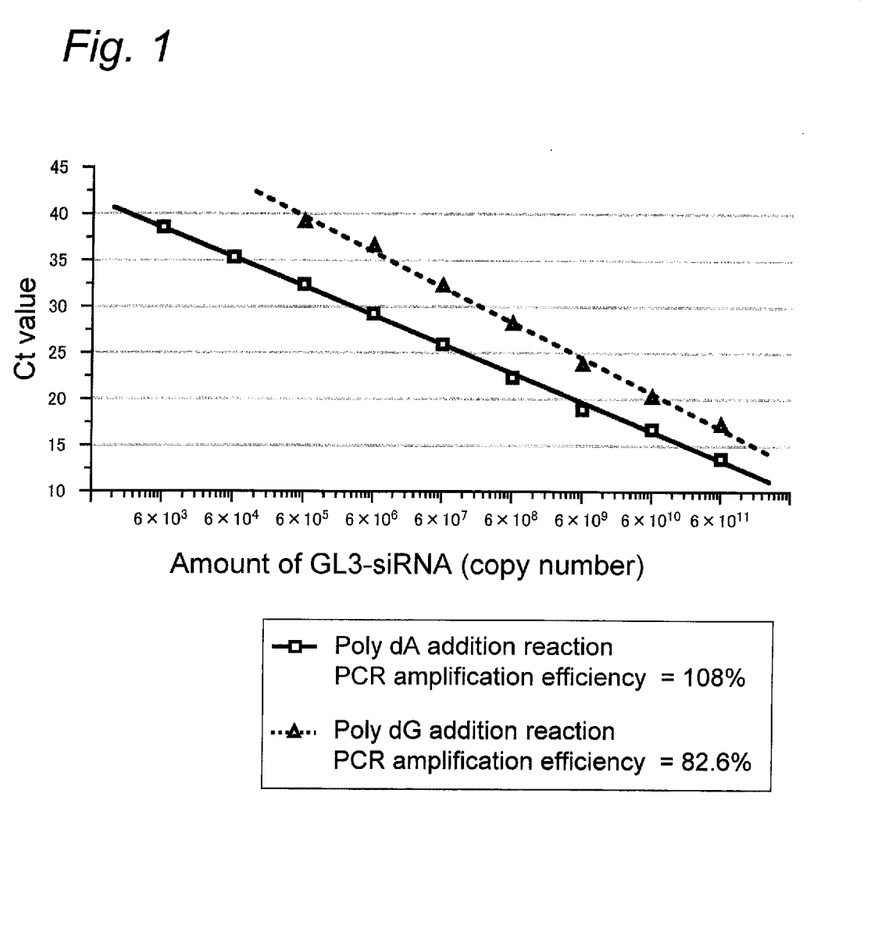
FIG. 1 is a view showing a calibration curve prepared by a method according to an exemplary embodiment of the present invention and a conventional method in which Ct values were obtained by quantifying siRNA in which the 3' end is DNA.

FIG. 1 shows a calibration curve prepared from Ct values (temperature cycle number when the amount of amplified nucleic acid reaches a certain level) obtained by real-time PCR and amounts of siRNA. The solid line represents a result quantified by using a poly dA addition reaction, while the broken line represents a result quantified by using a poly dG addition reaction. The PCR amplification efficiency was obtained from a slope of each calibration curve. Compared to the method for quantifying siRNA by using a poly dG addition reaction, a method for quantifying siRNA by using a poly dA addition reaction showed small Ct values and a value near 100 percent as the PCR amplification efficiency, and thus an ideal PCR amplification was considered to be achieved. This indicates that siRNA at broader range of $6\times10^3$ copy numbers (2 fM) to $6\times10^{11}$ copy numbers (200 nM) can be detected by the method of quantifying siRNA using a poly dA addition reaction, that is the method of the present invention, and a significant improvement in detection sensitivity was achieved according to the method of the present invention. An ideal PCR amplification, and detection in a broader concentration range was achieved, and thus the method for detecting siRNA according to the present invention is considered to show a high detection precision and a high reliability.

Example 2

Quantification Example of Synthetic siRNA by Poly dA Addition

PLK1-siRNA having sequences represented by SEQ ID NOs: 7 and 8 and MetLuc2-siRNA having sequences represented by SEQ ID NOs: 9 and 10 were synthesized to perform a poly dA addition reaction in the same manner as in the preparation of siRNA solution in Example 1-(1) and the DNA addition reaction in Example 1-(2).

Subsequently, 5 μL of 6 μM oligo dT primer (AA) (SEQ ID NO: 13) was added to 5 μL of a reaction solution subjected to poly dA addition reaction to make 10 μL of the mixed solution as a total volume. The resulting solution was subjected to heat treatment at 70° C. for 5 minutes, and then rapidly cooled on ice for an annealing. The siRNA used in the present experimental example has a structure having two dT bases projected at the 3' end, and thus the oligo dT primer (AA) having a sequence dA-dA complementary to the two projected bases of dT at the 3' end can anneal to a predetermined position. The oligo dT primer (AA) also has a poly dT region of 24 bases and a tag sequence region for PCR amplification at the 5' end.

The annealed reaction solution was subjected to a reverse transcription reaction at 42° C. for 15 minutes by using Blue-Print (trademark) RT reagent Kit (for Real Time) (manufactured by Takara Bio Inc.), and a single stranded DNA was synthesized under conditions allowing reverse transcriptase to be deactivated at 85° C. for 5 seconds.

Figure 2A:
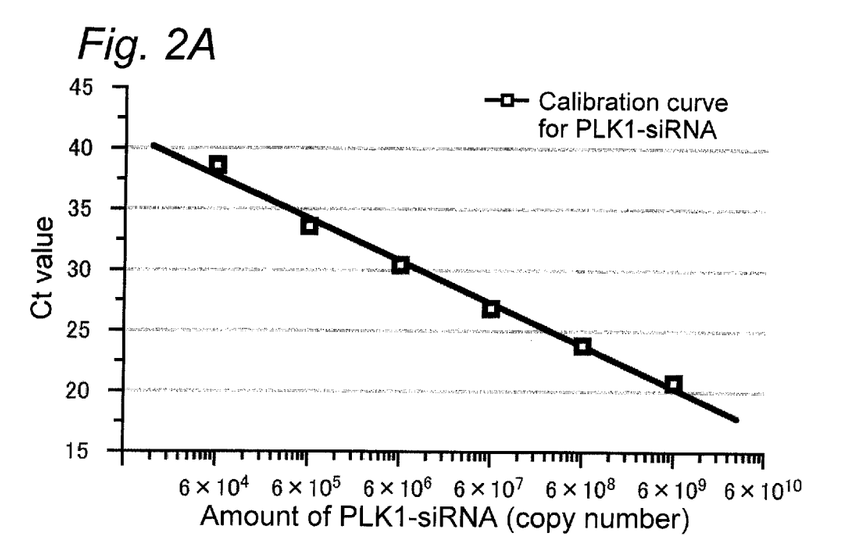
FIG. 2A is a view showing a calibration curve prepared by a method according to an exemplary embodiment of the present invention in which Ct values were obtained by quantifying PLK-siRNA in which the 3' end is DNA.
Figure 2B:
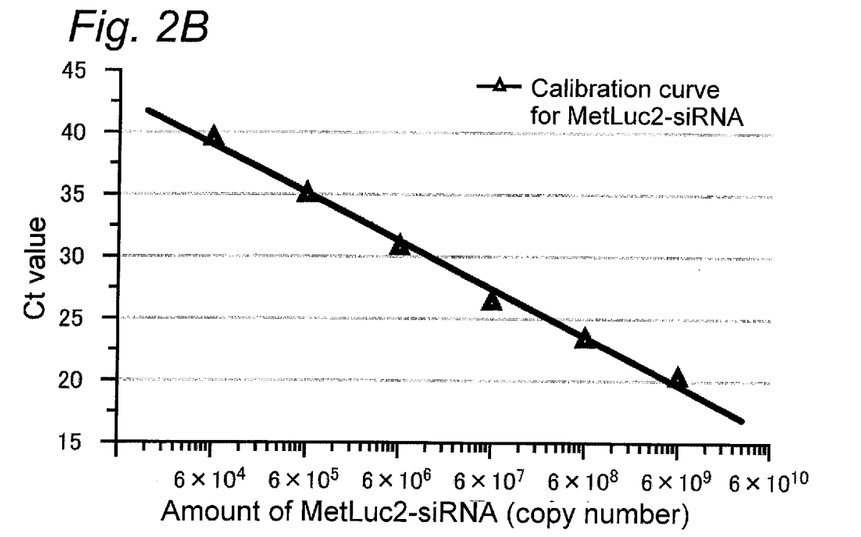
FIG. 2B is a view showing a calibration curve prepared by a method according to an exemplary embodiment of the present invention in which Ct values were obtained by quantifying MetLuc2-siRNA in which the 3' end is DNA.

The prepared DNA was used as a template to perform a real-time PCR as in Example 1-(4). The antisense-strand derived primers used in real-time PCR are shown in SEQ ID NO: 11 (PLK1-siRNA) and SEQ ID NO: 12 (MetLuc2-siRNA). Calibration curves were prepared from Ct values obtained and are shown in FIG. 2A and FIG. 2B. From FIG. 2A and FIG. 2B, siRNA at $6 \times 10^4$ copy numbers (20 fM) to $6 \times 10^9$ copy numbers (2 nM) could be detected even when these siRNAs were used, and the detection ranges were broad as in Example 1.

Example 3

Quantification Example of siRNA in a Total RNA Containing Sample

In order to confirm influences of RNA having poly A, such as a small molecule RNA or mRNA present in a total RNA on the reaction system, an artificially synthesized siRNA was quantified under conditions in which a certain amount of a total DNA was included.

A dilution series of GL3-siRNA was prepared in the same manner as in the method of preparing siRNA in Example 1-(1). Also, 40 ng/4 of an NIH3T3 cell-derived total RNA solution was used in the dilution, and thus 200 ng of the total RNA was added to 5 μL of a siRNA solution to be used in a DNA addition reaction.

Then, a single-stranded DNA was synthesized in the same manner as in Example 2, and subsequently, a real-time PCR was performed in the same manner as in amplification and detection of siRNA in Example 1-(4).

Figure 3:
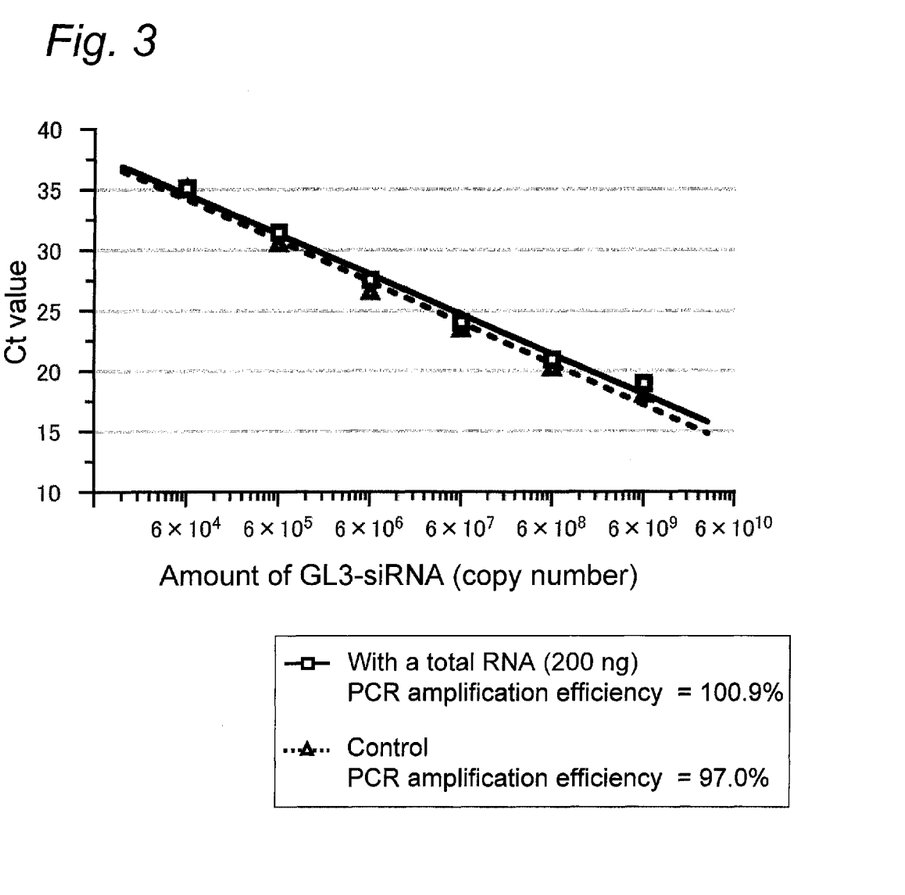
FIG. 3 is a view showing a calibration curve prepared by a method according to an exemplary embodiment of the present invention in which Ct values were obtained by quantifying siRNA in which the 3' end is DNA under the presence of total RNA.
Figure 4:
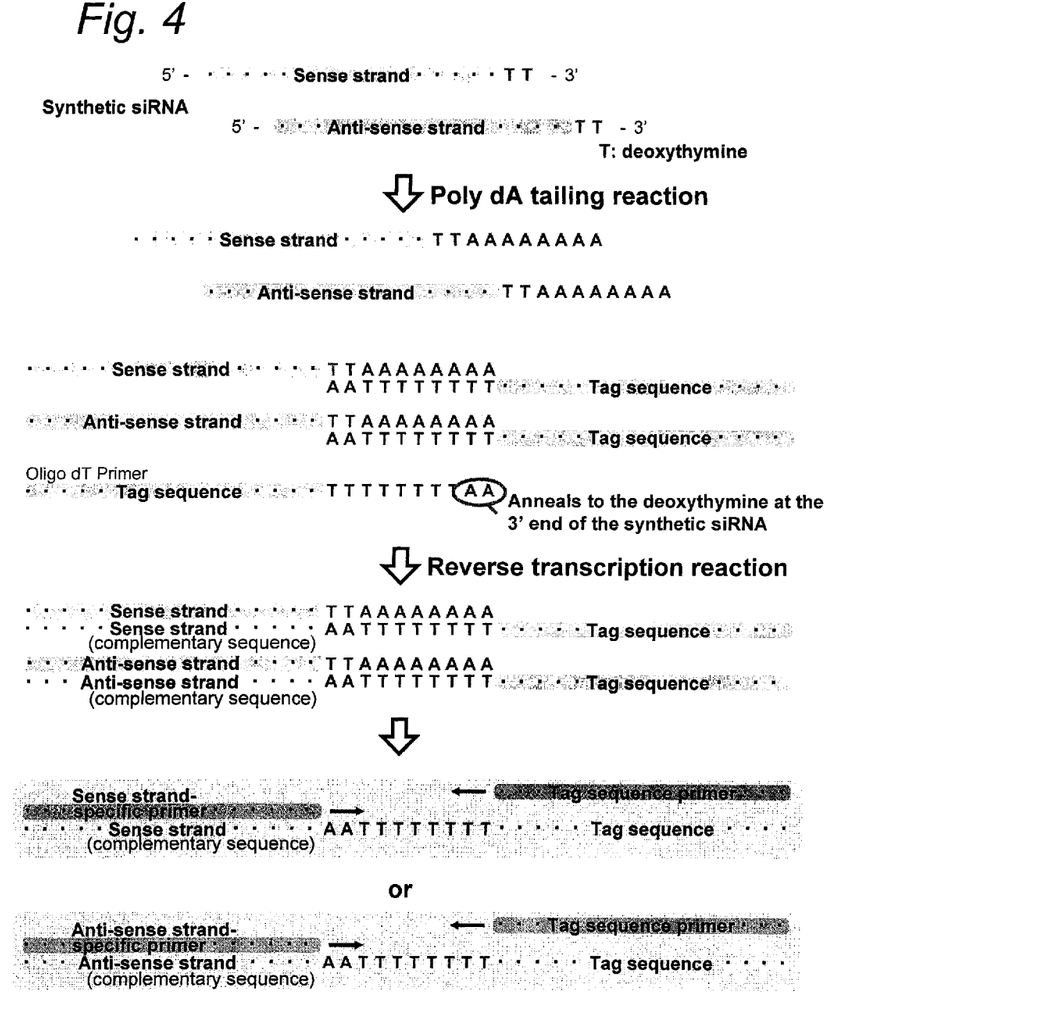
FIG. 4 is a schematic view of a method for detecting siRNA in which the 3' end is DNA according to an exemplary embodiment of the present invention.

A calibration curve was prepared from Ct values obtained and is shown in FIG. 3. From FIG. 3, influences of the total RNA on the reaction system were barely observed, compared to a control to which the total RNA was not added. Even when a sample containing extra RNA having poly A was used, siRNA at $6 \times 10^4$ copy numbers (20 fM) to $6 \times 10^9$ copy numbers (2 nM) could be detected, and the detection range was broad as in Example 1.

In the present invention, a method for accurately and easily detecting synthetic siRNA, for example, siRNA in which the 3' end is DNA, and a kit used for the method, are provided. The present invention may be used in a method for detecting siRNA in cells or the living body, and be very useful in basic studies and applied fields of medicine.

While the invention has been described in detail and with reference to specific embodiments thereof, it will be apparent to one skilled in the art that various changes and modifications can be made therein without departing from the scope thereof.

SEQUENCE LISTING FREE TEXT

SEQ ID NO:1: Synthetic oligonucleotide GL3-siRNA. Nucleotides 1 to 19 are ribonucleotides—other nucleotides are deoxyribonucleotides.

SEQ ID NO:2: Synthetic oligonucleotide GL3-siRNA. Nucleotides 1 to 19 are ribonucleotides—other nucleotides are deoxyribonucleotides.

SEQ ID NO:3: poly dA primer with tag sequence.

SEQ ID NO:4: Tag sequence primer.

SEQ ID NO:5: Antisense primer for GL3-siRNA.

SEQ ID NO:6: poly dC primer with tag sequence.

SEQ ID NO:7: Synthetic oligonucleotide PLK1-siRNA. Nucleotides 1 to 19 are ribonucleotides—other nucleotides are deoxyribonucleotides.

SEQ ID NO:8: Synthetic oligonucleotide PLK1-siRNA. Nucleotides 1 to 19 are ribonucleotides—other nucleotides are deoxyribonucleotides.

SEQ ID NO:9: Synthetic oligonucleotide MetLuc-siRNA. Nucleotides 1 to 19 are ribonucleotides—other nucleotides are deoxyribonucleotides.

SEQ ID NO:10: Synthetic oligonucleotide MetLuc-siRNA. Nucleotides 1 to 19 are ribonucleotides—other nucleotides are deoxyribonucleotides.

SEQ ID NO:11: Antisense primer for PLK1-siRNA

SEQ ID NO:12: Antisense primer for MetLuc-siRNA

SEQ ID NO:13: Oligo dT primer (AA)

What is claimed is:

1. A method for detecting a synthetic siRNA in which the 3' end is a $dT_{1-4}$ nucleotide sequence, comprising:
   (a) adding polydeoxyadenosine to the 3' DNA end of at least one strand of the siRNA to be detected to produce a polydeoxyadenosine-added RNA;
   (b) annealing a polydeoxythymidine primer having a tag sequence at its 5' end to the polydeoxyadenosine-added RNA and synthesizing DNA from the primer by reverse transcription; and
   (c) detecting the DNA synthesized in (b), wherein the polydeoxythymidine primer comprises in 3' to 5' direction a $dT_{1-4}$ nucleotide sequence, a polydeoxythymidine sequence, and the tag sequence, wherein the tag sequence distinguishes a polydeoxythymidine primer having the tag sequence at its 5' end from a polydeoxythymidine primer without the tag sequence, and wherein the step of detecting is performed by a nucleic acid amplification in (c) using the synthesized DNA as a template, and using a first primer comprising a sequence homologous to the tag sequence and a second primer comprising a sequence homologous to the strand of the siRNA to which the polydeoxyadenosine is added.

2. The method of claim 1, further comprising the step of quantifying the synthesized DNA to calculate an amount of the siRNA to which polydeoxyadenosine was added in (a).

3. The method of claim 1, wherein the polydeoxyadenosine is added in step (a) by a terminal deoxynucleotidyl transferase.

4. The method of claim 1, wherein the tag sequence is a universal tag sequence.

5. The method of claim 1 wherein 20 fM to 2 nM of siRNA can be measured.

* * * * *